United States Patent

Adachi et al.

[11] Patent Number: 5,294,598
[45] Date of Patent: Mar. 15, 1994

[54] HERBICIDAL 3-SUBSTITUTEDBENZOYL-BICYCLO[4,1,0-]HEPTANE-2, 4-DIONE DERIVATIVES

[75] Inventors: Hiroyuki Adachi; Katsunori Tanaka; Takashi Kawana; Hideo Hosaka, all of Odawara, Japan

[73] Assignee: Nippon Soda Co., Ltd., Tokyo, Japan

[21] Appl. No.: 819,150

[22] Filed: Jan. 9, 1992

Related U.S. Application Data

[63] Continuation-in-part of Ser. No. 651,266, Jun. 29, 1990, Pat. No. 5,228,898.

[30] Foreign Application Priority Data

Jun. 4, 1991 [JP] Japan ............... 3-159689
Jul. 9, 1991 [JP] Japan ............... 3-193595

[51] Int. Cl.$^5$ ............... A01N 41/00; C07C 317/14
[52] U.S. Cl. ............... 504/315; 560/11; 562/427; 568/31
[58] Field of Search ............... 560/11; 568/31; 71/103; 562/427; 504/315

[56] References Cited

U.S. PATENT DOCUMENTS

| | | | |
|---|---|---|---|
| 4,681,621 | 7/1987 | Lee et al. | 71/103 |
| 4,781,751 | 11/1988 | Chin | 71/103 |
| 4,783,213 | 11/1988 | Lee | 71/98 |
| 4,806,146 | 2/1989 | Carter | 71/98 |
| 4,869,748 | 9/1989 | Knudsen | 71/123 |
| 4,943,310 | 7/1990 | Angermann et al. | 71/88 |
| 4,954,165 | 9/1990 | Baba et al. | 71/103 |

*Primary Examiner*—José G. Dees
*Assistant Examiner*—Vera C. Clarke
*Attorney, Agent, or Firm*—Joseph C. Mason, Jr.; Ronald E. Smith

[57] ABSTRACT

This invention relates to 3-substitutedbenzoyl-bicyclo[4,4,0]heptane-2,4-dione with high herbicidal activity represented by formula I

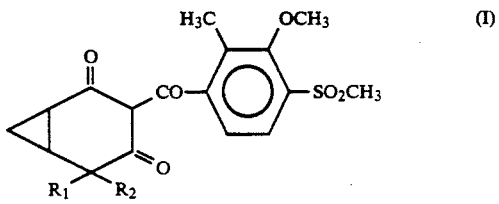

wherein one of $R_1$ or $R_2$ represents methyl and the other represents hydrogen or lower alkyl or alkoxycarbonyl or its salt.

16 Claims, No Drawings

HERBICIDAL 3-SUBSTITUTEDBENZOYL-BICYCLO[4,1,0]HEPTANE-2, 4-DIONE DERIVATIVES

This is a continuation-in-part of copending application Ser. No. 07/651,266 filed on Jun. 29, 1990, now U.S. Pat. No. 5,228,898.

FIELD OF INVENTION

This invention relates to 3-substitutedbenzoyl-bicyclo[4,1,0]heptane-2,4-dione derivatives and a herbicide containing them.

DESCRIPTION OF RELATED ART

To save vast laboring effort to control weeds in agricultural and horticultural cultivation, many kinds of herbicides have been applied. However, they have caused to be phytotoxic for edible crops and/or environmental pollution problem owing to their persistence. Therefore, a new herbicide which is sufficiently effective at lower dosage and is safe to use has been needed. Prior art patents of interest include DE390218, U.S. Pat. No. 4,921,526, and PCT Application No. WO91/00260.

SUMMARY OF THE INVENTION

An object of the invention is to provide a herbicidal compound that is highly effective to control major weeds with selectivity for corn.

Compounds in the present invention are represented by the following formula

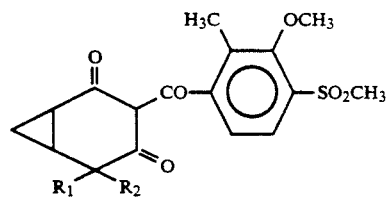

wherein one of $R_1$ or $R_2$ represents methyl and the other represents hydrogen, or lower alkyl or alkoxycarbonyl and their salts.

These compounds are able to be synthesized by the following methods;

Preparation Method a.

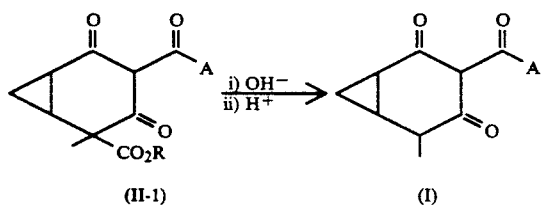

-continued
Preparation Method

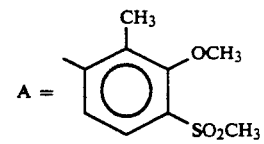

b.

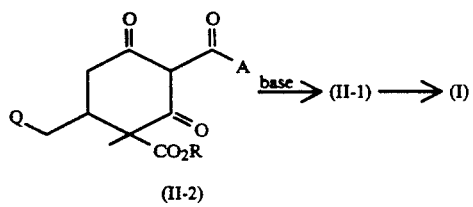

c.

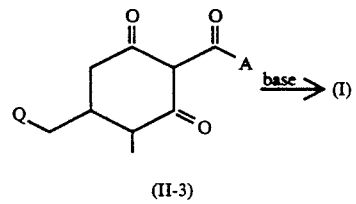

wherein R is alkyl, Q is a leaving group such as halogen, alkylsulfonate or aryl sulfonate, etc.

Preparation Method a

Compound II-1 is hydrolyzed in a solvent in the presence of a base. The base used is alkali metal hydroxide such as NaOH or KOH, etc., alkali metal carbonate or alkali earth metal hydroxide, etc. The solvent used is water or if necessary, alcohol, dichloromethane, toluene, THF or DMF, etc. with it. After hydrolyzing, the product is neutralized and decarboxylated adding hydrochloric acid or sulfuric acid. Then, desired compound [I] is obtained.

Preparation Method b

Compound II-1 is obtained by reaction of compound II-2 with 2 moles or more excess of a base at −20° C. to boiling point of used solvent, desirably 0° C. to 50° C., for 30 minutes to several tens e.g. 16 hours. The base used is hydroxide of alkali metal such as KOH or NaOH, and of alkali earth metal, tri(C1–C8 alkyl)amine, pyridine, DBI, t-BuOK, Triton B, sodium carbonate or sodium phosphate, etc. The solvent used is water, alcohol, dichloromethane, benzene, toluene, ethyl acetate, dimethylformamide, THF, dimethoxyethane or acetonitrile, etc. The desired compound [I] is then obtained as in preparation method a.

Preparation Method c

The desired compound [I] is produced from compound [II-3] according to the preparation method b.

In the above descriptions the starting material used in these processes is prepared by the following method.

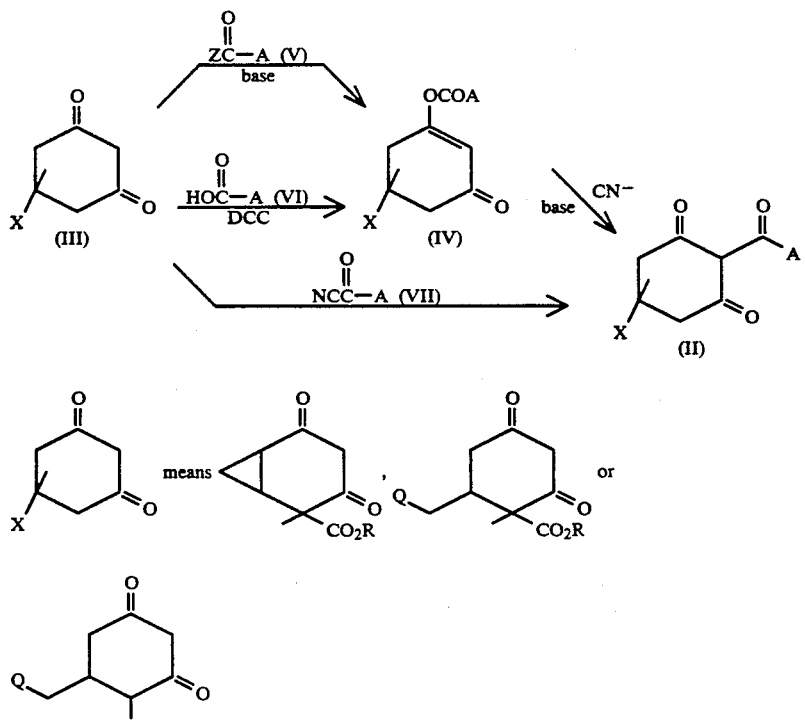

wherein Z is a leaving group such as halogen, alkylcarbonyloxy, alkoxycarbonyloxy or benzoyloxy, etc. and A, Q and R are the same groups as in the preceding description.

Compound IV is obtained by a reaction of each 1 mol of compound [III] and compound [V] in the presence of 1 mol or more excess of a base, or each 1 mol of compound [III], compound [VI] and 1 mol or more excess of cyclohexylcarbodimide. The base used is hydroxide of alkali metal such as KOH or NaOH, and of alkali earth metal, tri(C1-C8 alkyl) amine, pyridine, sodium carbonate, or sodium phosphate, etc. The solvent used is water, alcohol, dichloromethane, toluene, ethyl acetate, dimethylformamide, THF, dimethoxyethane or acetonitrile, etc. The reaction mixture is stirred to complete the reaction at 0° C.-50° C. The compound (IV) is also obtained by a reaction in two-phase using a phase transfer catalyst such as BTEAC.

The solvent used in the reaction with DCC is dichloromethane, toluene, ethyl acetate, dimethylformamide, THF, dimethoxyethane or acetonitrile, etc. The mixture is stirred to complete the reaction at 0° C.-50° C. The reaction mixture is treated by ordinary method.

Rearrangement reaction is carried out in the presence of cyano compound and a moderate base. The compound above mentioned, for example, 1 mol of compound [IV] is reacted with 1-4 mol, desirably 2 moles, of a base and 0.01-0.5 mole or more, desirably 0.1 mole of a cyano compound. The base used in this case may be the same one as described above. Potassium cyanide, acetone cyanhydrin, hydrogen cyanide or a polymer immobilizing potassium cyanide, etc., may be the cyano compound used in this case.

Furthermore, the reaction is accelerated by the addition of a small amount of phase transfer catalyst such as crown ether, etc. The reaction temperature is kept at lower than 80° C., desirably 20° C. to 40° C. The solvent used is 1,2-dichloroethane, toluene, acetonitrile, dichloromethane, ethyl acetate, dimethylformamide methyl isobutyl ketone, THF or dimethoxyethane, etc.

Compound [II] is also obtained by reaction between compound [III] and [VII] in the presence of a base and a Lewis acid.

The base used is hydroxide of alkali metal such as KOH or NaOH, and of alkali earth metal, tri(C1-C8 alkyl)amine, pyridine, sodium carbonate, or sodium phosphate, etc. The appropriate Lewis acid is zinc chloride or aluminum trichloride, etc., desirably zinc chloride. The reaction is carried out in a organic solvent such as acetonitrile or dichloromethane, etc., at proper temperature of 20° C. to 40° C.

It is suitable that zinc chloride and a base are slightly excess for compound [III].

Stereoisomers exist in the compound [I] synthesized by such methods because of the relation between of methyl at 5-position and cyclopropane ring. Trans isomer is usually formed in the preparation method c, while the stereoisomer desired can be obtained by selection of starting material in the method a or b, because the stereo specificity of the material is held through the reactions.

Additionally, optical isomers exist in the starting materials and the invented compounds [I], and many types of tautomeric isomer also exist in them, as shown below.

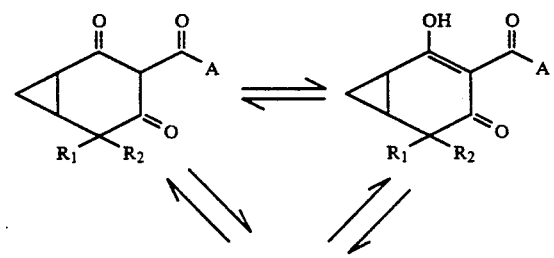

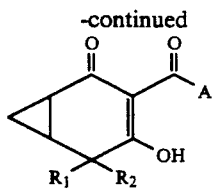

wherein A is the same as above mentioned. These types are within in the scope of the present invention.

The salts of compounds [I] and II-1] are especially useful for agriculturally and horticulturally applications including allowable salts, enamines, their analogues, acrylates, sulfonates, carbamates or ethers.

Sodium, potassium, calcium, ammonium, or the like are the salts to be agriculturally and horticulturally allowable. An ion of a structural formula:$N^+ R^a R^b R^c R^d$ (wherein each $R^a R^b R^c$ and $R^d$ are respectively selected from hydrogen and C1–C10 alkyl groups which may be substituted by, for example, hydroxyl group in some cases) is given as an example. This desirably contains 1–4 carbon atoms if any of $R^a R^b R^c$ and $R^d$ are substituted alkyl in some cases.

The proper enamines or their analogues are compounds in which each OH group is converted to group represented by formula: $-NR^e R^f$ (wherein $R^e$ is C1–C6 alkyl or aryl, substituted according to case, for example, phenyl. $R^f$ is hydrogen or C1–C6 alkyl or aryl, substituted according to case, for example, phenyl.), halogen or $SR^a$.

The proper acrylate or ether derivatives are compound in which the OH part is converted to group represented by a formula: $-OCOR^h$ or $OR^h$ wherein $R^h$ is same group as above $R^e$.

The proper carbamate derivatives are compounds in which OH part is converted to group represented by a formula: $-OC(O)NR^i R^j$ (wherein each $R^i$ and $R^j$ is hydrogen or same group as above $R^e$).

These derivatives can be prepared by usual methods.

DESCRIPTION OF THE PREFERRED EMBODIMENTS

The compounds of the invention are described in detail in the following examples. Structure of the invented compound is identified by IR, NMR and MS analysis, etc.

EXAMPLE 1

Synthesis of 3-(3-Methoxy-2-methyl-4-methylsulfonylbenzoyl)-trans-5-ethoxycarbonyl-cis-5-methyl-cis-bicyclo[4,1,0-]heptane-2,4-dione

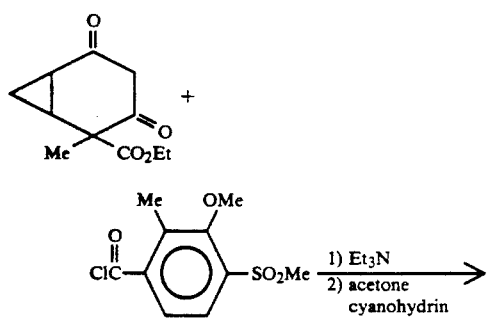

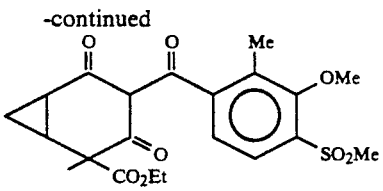

To a solution of 12.1 g (58.0 mmol) of trans-5-ethoxycarbonyl-cis-5-methyl-cis-bicyclo[4,1,0]heptane-2,4-dione and 15.2 g (58.0 mmol) of 3-methoxy-2-methyl-4-methylsulfonylbenzoyl chloride in 150 ml of dichloromethane cooled by ice water bath. 7.02 g (69.6 mmol) of triethylamine was added dropwise with stirring, then the mixture was stirred at r.t. for 1 hour. The reaction mixture was washed with 2N hydrochloric acid and, then with water, and dried over anhydrous magnesium sulfate and concentrated to dryness to give an oily crude product.

The residue was dissolved in 150 ml of acetonitrile and then 8.73 g (69.9 mmol) of trimethylamine and 1.47 g (17.3 mmol) of acetone cyanohydrin were added at room temperature. The mixture was reacted at r.t. for 16 hours. After the reaction was completed, 2N hydrochloric acid and dichloromethane were added to the reaction mixture. The organic layer was washed with saturated aqueous sodium chloride, dried over anhydrous magnesium sulfate and concentrated to dryness to give 23.6 g (93.3%) of desired compound as crude crystal. m.p. 115°–117° C.

EXAMPLE 2

3-(3-methoxy-2-methyl-4-methylsulfonylbenzoyl)-cis-5-methyl-cis-bicyclo[4,1,0]heptane-2,4-dione

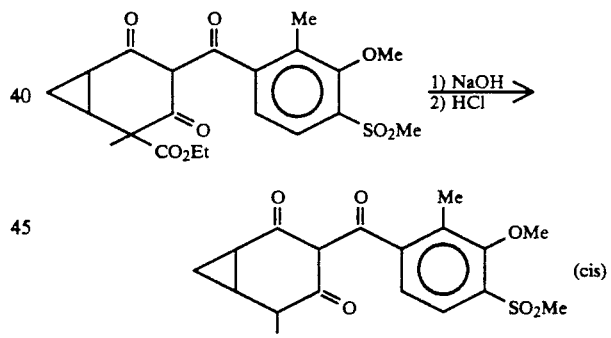

9.08 g (20.8 mmol) of 3-(3-methoxy-2-methyl-4-methylsulfonylbenzoyl)-trans-5-ethoxycarbonyl-cis-5-methyl-bicyclo[4,1,0]heptane-2,4-dione was dissolved in 90 ml of dichloromethane to which 62.4 ml (62.4 mmol) of 1N sodium hydroxide aqueous solution was added at room temperature and resulting mixture stirred for 16 hours. After the hydrolysis was completed, to the reaction mixture was added 50 ml of ice water and then the mixture was neutralized and decarboxylated with 1N-HCl under cooling with ice-water. After reacting for 1 hour 1N 20.8 ml (20.8 mmol) of hydrochloric acid was added again to the reaction mixture and then organic layer was washed with water and dried over anhydrous magnesium sulfate. The solvent was distilled. The residue was recrystallized from methanol. Thus, 6.40 g (84.5%) of the desired compound was obtained as white crystal.

m.p. 152°–155° C.

EXAMPLE 3

3-(3-methoxy-2-methyl-4-methylsulfonylbenzoyl)-trans-5-methyl-cis-bicyclo[4,1,0]heptane-2,4-dione

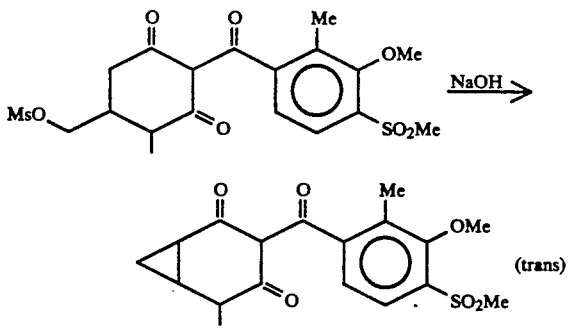

1.0 g (2.17 mmol) of 5-mesyloxymethyl-2-(3-methoxy-2-methyl-4-methylsulfonylbenzoyl)-4-methylcyclohexane-1,3-dione was dissolved in 10 ml of ethanol, and reacted with adding 6.5 ml (6.5 mmol) of 1N sodium hydroxide aqueous solution at room temperature with stirring for 16 hours. After the reaction was completed, 10 ml of 2N hydrochloric acid was added in the reaction mixture, which is extracted by ethyl acetate. After the organic layer was washed with aqueous solution of sodium hydroxide, the organic layer was dried over anhydrous magnesium sulfate. The solvent was distilled. The residue was recrystallized from methanol. Thus, 0.18 g (22.9%) of the desired compound was obtained as white crystal.

m.p. 169°-170° C.

EXAMPLE 4

Sodium salt of 3-(3-methoxy-2-methyl-4-methylsulfonylbenzoyl)-cis-5-methyl-cis-bicyclo[4,1,0]heptane-2,4-dione

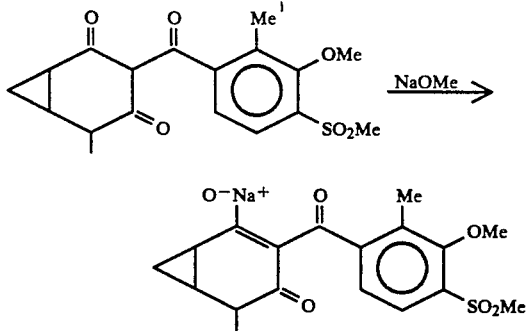

0.21 g (0.52 mmol) of 3-(3-methoxy-2-methyl-4-methylsulfonylbenzoyl)-cis-5-methyl-cis-bicyclo[4,1,0-]heptane-2,4-dione was dissolved in 10 ml of dichloromethane, then, 0.10 g (0.52 mmol) of 28% sodium methylate was added and stirred for 1 hour at room temperature. The residue was concentrated and washed with ethyl ether to obtain the desired compound, as 0.20 g (99%) of white crystal.

m.p. higher than 230° C.

A herbicidal composition of the present invention, containing one or more compounds represented by formula (I) as the active ingredients, is similar as common pesticide formulation type in which active ingredient is blended with proper carriers to formulate wettable powder, emulsifiable concentrate, dust, granule and soluble powder or flowable for use. As solid carrier or diluent, talc, white carbon (silica), bentonite, clay, and diatomaceous earth may be used. As liquid carrier or diluent, water, alcohol, benzene, xylene, kerosene, mineral oil, cyclohexane, clyclohexanone and dimethylformamide may be used. If necessary, in order to give a homogeneous and stable formulation, a surface active agent may be added.

Concentration of active ingredient of the herbicide on the present invention is dependent upon the formulation type. For example, it is generally used that 5-70%, desirably, 10-30% for wettable powder; 3-70%, desirably, 5-20%, for emulsifiable concentrate; 0.01-30%, desirably, 0.05-10% for granular formulation.

The wettable powder and emulsifiable concentrate obtained as described above are diluted by water to the desired concentration and used as aqueous suspension or aqueous emulsion for treating on soil including pre- and post-emergence of weeds or to their foliage. Furthermore, granular formulation may be directly treated same manner as above. In practical use, the herbicide containing the invented compound at appropriate dosage rate of 10 g/ha as the active ingredient or more may be applied to the habitat.

Furthermore, the herbicide containing the invented compound can be applied admixed with known agricultural chemicals such as fungicides, insecticides, herbicides and plant growth regulators. One result from such admixing with another herbicide may be that the herbicides are not only saved in dosage but also through synergistic action to achieve savings in labor.

Multiple combinations of another herbicide with the invented compound are possible in some cases, in which appropriate herbicides type of carbamates and thiocarbamates such as benthiocarb, molinate, dimepiperate, etc., acid amides herbicides butachlor, pretilachlor, mefenacet etc., diphenyl ethers such as chlometoxinil, bifenox, etc., triazines such as atrazine, cyanazine, etc., sulfonylureas such as chlorosulfuron, sulfomethuron-methyl, etc., phenoxyalkane carboxylic acids such as MCP, MCPB, etc., phenoxyphenoxy propionic acids such as dichlofop-methyl, etc., pyridyloxyphenoxy propionic acids such as fluazifop-butyl, etc., benzoylaminopropionic propionic acids such as benzoylprop-ethyl, flamprop-ethyl, etc., others such as piperophos, dymuron, bentazone, difenzoquat, naproanilid, HW-52 (4-ethoxymethoxybenzo-2,3-dichloroanilide), KNW-242 [1-(3-methyl-phenyl)-5-phenyl-1H-1,2,4-triazole-3-carboxamide], quinclorac (3,7-dichloro-8-quinoline carboxylic acid) and cyclohexanediones such as sethoxydim, alloxydim-sodium etc., are given as examples. Vegetable oil or crop oil concentrate is also possible to be added in the admixture.

Several examples of herbicidal compositions containing to the invented compounds are shown, but both proportions of compounds as active ingredient and inactive additives are not limited in the description hereafter and widely variable.

EXAMPLE 5

Wettable Powder

|  | Parts by Weight |
| --- | --- |
| Compound of this invention | 20 |
| White carbon (silica) | 2 |
| Diatomaceous earth | 70 |
| Sodium alkylsulfate | 2 |

-continued

| | Parts by Weight |
|---|---|
| Sodium lignin sulfonate | 6 |

These are homogeneously mixed and pulverized to obtain a wettable powder containing 20% of active ingredient.

EXAMPLE 6

Emulsifiable Concentrate

| | Parts by Weight |
|---|---|
| Compound of this invention | 20 |
| Xylene | 55 |
| Dimethylformamide | 15 |
| polyoxyethylene phenyl ether | 10 |

These are mixed and dissolved to obtain an emulsifiable concentrate containing 20% of active ingredient.

Test 1: Postemergence Treatment

Herbicidal effects are shown in following test examples. Seeds of crabgrass (*Digitalia sanguinalis*), giant foxtail (*Setaria faberi*), redroot pigweed (*Amaranthus retroflexus*), velvetleaf (*Abutilon theophlasti*) and purple nutsedge (*Cyprus rotundus*) were planted at upper layer of soil packed in 200 cm² pot, lightly covered by soil and grown in green house. When each weed was grown to 5–10 cm in height, 125 ppm of aqueous dilution of emulsifiable concentrate of each test compound was sprayed to stem and foliar part of the weed at the rate of 1000 l/ha (that means 125 g of active ingredient/ha). Three weeks after spraying the degree of damage to each weed was evaluated by the following criteria. The results are shown in Table 1.

Damage Evaluation Criteria

| % of killed weed | Herbicidal Index |
|---|---|
| 0 | 0 |
| 20–29 | 2 |
| 40–49 | 4 |
| 60–69 | 6 |
| 80–89 | 8 |
| 100 | 10 |

Additionally, FIGS. 1, 3, 5, 7 or 9 indicates the middle index between 0 and 2, 2 and 4, 4 and 6, 6 and 8 or 8 and 10, respectively.

% of killed weed = [(fresh weight of foliage of the weed untreated) − (that of treated)]/(fresh weight foilage of the weed untreated) × 100

TABLE 1

| Compound | Active ingredient g/ha | Herbicidal Index | | | | | |
|---|---|---|---|---|---|---|---|
| | | Henry crabgrass | giant foxtail | velvet-leaf | redroot pigweed | rice flatsedge | corn |
| compound of Example 1 | 125 | 10 | 10 | 10 | 10 | 10 | 0 |
| compound of Example 2 | 125 | 10 | 10 | 10 | 10 | 10 | 0 |
| compound of Example 3 | 125 | 10 | 10 | 10 | 10 | 10 | 0 |
| comparative compound A | 125 | 4 | 5 | 8 | 3 | 4 | 4 |
| comparative compound B | 125 | 2 | 0 | 0 | 0 | 2 | 0 | comparative compound A:

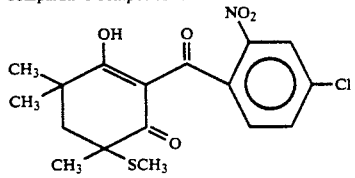

(compound described in DE 3902818)

comparative compound B:

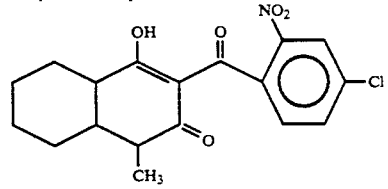

(compound described in U.S. Pat. No. 4921526)

We claim:
1. Compound of the formula

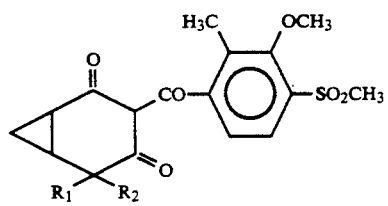

or an optical isomer or a salt thereof, wherein one of $R_1$ or $R_2$ represents methyl and the other represents hydrogen or lower alkoxycarbonyl.

2. Compound of the formula

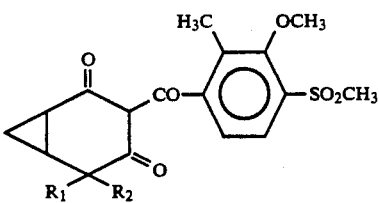

or an optical isomer or a salt thereof, wherein $R_1$ is methyl and $R_2$ is ethoxycarbonyl.

3. Compound of the formula

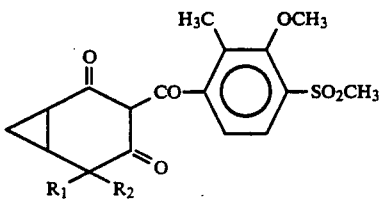

or an optical isomer or a salt thereof, wherein $R_1$ is methyl and $R_2$ is hydrogen.

4. Herbicidal composition comprising a herbicidally effective amount of a compound of the formula

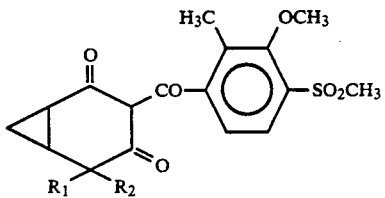

or an optical isomer or a salt thereof, wherein one of $R_1$ or $R_2$ represents methyl and the other represents hydrogen or lower alkoxycarbonyl.

5. Herbicidal composition comprising a herbicidally effective amount of a compound of the formula

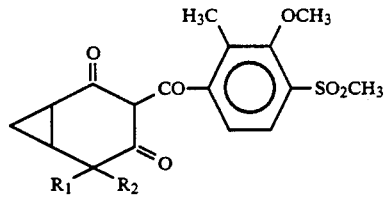

or an optical isomer or a salt thereof, wherein $R_1$ is methyl and $R_2$ is ethoxycarbonyl, and an inert carrier therefor.

6. Herbicidal composition comprising a herbicidally effective amount of a compound of the formula

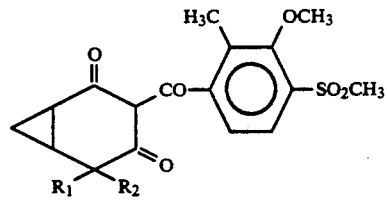

or an optical isomer or a salt thereof, wherein $R_1$ is methyl and $R_2$ is hydrogen, and an inert carrier therefor.

7. Method of controlling weed pests which comprises adding to the habitat thereof a herbicidally effective amount of the composition according to claim 4.

8. Compound 3-(3-methoxy-2-methyl-4-methylsulfonylbenzoyl)-trans-5-ethoxycarbonyl-cis-5-methyl-cis-bicyclo[4,1,0]heptane-2,4-dione.

9. Compound 3-(3-methoxy-2-methyl-4-methylsulfonylbenzoyl)-cis-5-methyl-cis-bicyclo[4,1,0]heptane-2,4-dione.

10. Compound 3-(3-methoxy-2-methyl-4-methylsulfonylbenzoyl)-trans-5-methyl-cis-bicyclo[4,1,0]heptane-2,4-dione.

11. Herbicidal composition comprising a herbicidally effective amount of the compound of claim 8 and a herbicidally acceptable carrier.

12. Herbicidal composition comprising a herbicidally effective amount of the compound of claim 9 and a herbicidally acceptable carrier.

13. Herbicidal composition comprising a herbicidally effective amount of the compound of claim 10 and a herbicidally acceptable carrier.

14. Method of controlling weed pests and protecting corn plants which comprises adding to the habitat thereof a herbicidally effective amount of the compound of claim 8 in a herbicidally acceptable carrier.

15. Method of controlling weed pests and protecting corn plants which comprises adding to the habitat thereof a herbicidally effective amount of the compound of claim 9 in a herbicidally acceptable carrier.

16. Method of controlling weed pests and protecting corn plants which comprises adding to the habitat thereof a herbicidally effective amount of the compound of claim 10 in a herbicidally acceptable carrier.

* * * * *